(12) United States Patent
Lee et al.

(10) Patent No.: US 8,813,517 B2
(45) Date of Patent: *Aug. 26, 2014

(54) AIR CONDITIONER AND AIR CONDITIONING SYSTEM

(75) Inventors: Sunghwa Lee, Changwon (KR); Younghoon Kim, Changwon (KR); Bongjo Sung, Changwon (KR); Jongho Park, Changwon (KR)

(73) Assignee: LG Electronics Inc., Seoul (KR)

( * ) Notice: Subject to any disclaimer, the term of this patent is extended or adjusted under 35 U.S.C. 154(b) by 782 days.

This patent is subject to a terminal disclaimer.

(21) Appl. No.: 12/919,447

(22) PCT Filed: Jul. 2, 2008

(86) PCT No.: PCT/KR2008/003887
§ 371 (c)(1),
(2), (4) Date: Aug. 25, 2010

(87) PCT Pub. No.: WO2009/110661
PCT Pub. Date: Sep. 11, 2009

(65) Prior Publication Data
US 2011/0005261 A1  Jan. 13, 2011

(30) Foreign Application Priority Data
Mar. 7, 2008  (KR) .................. 10-2008-0021234

(51) Int. Cl.
*F25B 41/00* (2006.01)
*F25D 31/00* (2006.01)

(52) U.S. Cl.
USPC ............... 62/274; 62/291; 62/304; 62/176.6; 62/126; 62/186; 236/51; 261/152; 261/153; 174/1

(58) Field of Classification Search
USPC ......... 62/274, 291, 91, 92, 93, 304, 314, 262, 62/263; 236/44 C, 51; 700/276, 278, 299, 700/300; 261/152, 153, 30, 91, 92
See application file for complete search history.

(56) References Cited

U.S. PATENT DOCUMENTS

| | | | |
|---|---|---|---|
| 2,327,242 A | 8/1943 | Bolcom | |
| 2,638,644 A * | 5/1953 | Rauhut | 96/142 |
| 3,733,062 A | 5/1973 | Bracich | |
| 3,823,926 A * | 7/1974 | Bracich | 261/106 |
| 3,951,625 A | 4/1976 | Follette | |
| 4,222,971 A | 9/1980 | Eilert | |

(Continued)

FOREIGN PATENT DOCUMENTS

| | | |
|---|---|---|
| CN | 1081306 | 1/1994 |
| CN | 1724949 | 1/2006 |

(Continued)

OTHER PUBLICATIONS

European Search Report dated Oct. 20, 2011.

(Continued)

*Primary Examiner* — Cheryl J Tyler
*Assistant Examiner* — Antonio R Febles
(74) *Attorney, Agent, or Firm* — KED & Associates, LLP (57) ABSTRACT

An air conditioner including a humidifier and an air conditioning system. The humidifier is modularized within the air conditioner so that the air conditioner performs humidifying together with air conditioning. Further, the humidifier may be linked in operation to the air conditioner.

10 Claims, 8 Drawing Sheets

(56) References Cited

U.S. PATENT DOCUMENTS

| | | | |
|---|---|---|---|
| 4,237,080 A | 12/1980 | Elliott | |
| 4,507,937 A * | 4/1985 | Bretz | 62/298 |
| 4,520,864 A * | 6/1985 | Katagiri et al. | 165/60 |
| 4,686,069 A * | 8/1987 | Hahne et al. | 261/92 |
| 4,976,113 A * | 12/1990 | Gershuni et al. | 62/314 |
| 5,589,132 A | 12/1996 | Zippel | |
| 5,728,288 A | 3/1998 | Kubo | |
| 5,862,673 A * | 1/1999 | Bang | 62/158 |
| 5,972,196 A | 10/1999 | Murphy et al. | |
| 6,077,479 A | 6/2000 | Milde et al. | |
| 6,371,450 B1 | 4/2002 | Davis et al. | |
| 6,451,364 B1 | 9/2002 | Ito | |
| 6,832,753 B1 | 12/2004 | Huang | |
| 6,863,715 B2 | 3/2005 | Ike et al. | |
| 7,101,491 B2 | 9/2006 | Nonoyama et al. | |
| 2003/0072675 A1* | 4/2003 | Takeda et al. | 422/22 |
| 2004/0129578 A1 | 7/2004 | McLachlan et al. | |
| 2005/0034978 A1 | 2/2005 | Kazi et al. | |
| 2005/0277381 A1* | 12/2005 | Banerjee et al. | 454/229 |
| 2008/0028771 A1* | 2/2008 | Nagae | 62/78 |
| 2009/0140060 A1* | 6/2009 | Stoner et al. | 236/51 |
| 2009/0242651 A1* | 10/2009 | Ha et al. | 236/51 |

FOREIGN PATENT DOCUMENTS

| | | | | |
|---|---|---|---|---|
| CN | 1749662 | | 3/2006 | |
| CN | 200947636 | | 9/2007 | |
| CN | 200979261 | | 11/2007 | |
| DE | 44 40 813 | | 5/1995 | |
| EP | 1 293 216 | | 3/2003 | |
| EP | 1 728 521 | | 12/2006 | |
| EP | 2 033 708 | | 3/2009 | |
| EP | 1 629 898 | | 9/2009 | |
| JP | 61237941 A | * | 10/1986 | F24F 6/00 |
| JP | 2001059638 A | * | 3/2001 | F24F 6/00 |
| JP | 2002071173 A | * | 3/2002 | F24F 6/00 |
| JP | 2002089937 A | * | 3/2002 | F24F 6/00 |
| JP | 2002089942 A | * | 3/2002 | F24F 6/00 |
| JP | 2003-172531 | | 6/2003 | |
| JP | 2004-358358 | | 12/2004 | |
| JP | 2005-003304 | | 1/2005 | |
| JP | 2005-090832 | | 4/2005 | |
| JP | 2005-114276 | | 4/2005 | |
| JP | 2005-135716 | | 5/2005 | |
| KR | 10-1993-0022020 | | 11/1993 | |
| KR | 10-2001-0028455 | | 4/2001 | |
| KR | 10-0309551 | | 9/2001 | |
| KR | 10-2002-0004258 | | 1/2002 | |
| KR | 10-2003-0067605 | | 8/2003 | |
| WO | WO 00/45457 | | 8/2000 | |

OTHER PUBLICATIONS

Chinese Office Action dated Oct. 26, 2011.
International Search Report dated Oct. 7, 2010.
European Search Report dated May 27, 2011 (Application No. 08778550.7).
International Search Report issued in PCT/KR2008/003885 dated Jan. 16, 2009.
European Search Report dated Jun. 22, 2011.
U.S. Office Action issued in U.S. Appl. No. 12/919,429 dated Sep. 25, 2012.
U.S. Office Action issued in U.S. Appl. No. 12/919,438 dated Dec. 31, 2012.
Chinese Office Action Sep. 28, 2012.
Chinese Office Action Oct. 9, 2012.
Korean Office Action dated May 28, 2014.

* cited by examiner

Fig. 10

AIR CONDITIONER AND AIR CONDITIONING SYSTEM

TECHNICAL FIELD

The present disclosure relates to an air conditioner and an air conditioning system.

BACKGROUND ART

Recently, many sterilizing methods and sterilizing apparatuses have been introduced that sterilize water in a preliminary stage by introducing gases with strong sterilizing properties, such as hydroxyl radicals (OH), active oxygen (O—, O2, O3), and hydrogen peroxide (H2O2) into water, and supplying the sterilized water to a certain compartment or item to sterilize the latter. Such sterilized water is useful in sterilizing applications for the food processing and distribution industry, animal husbandry, hospitals, and other fields that require sterilization.

Also, there are many efforts currently underway to combine household appliances (such as air conditioners with heater/cooler functions, air cleaners, and humidifiers) with in-water discharging technology to maintain indoor air in a clean state by removing bacteria and viruses from water.

A method based on the bubble mechanism theory discharges bubbles of active oxygen and ozone, using a discharge cell with electrodes immersed in water to generate short bursts of powerful electric fields at the discharge cell and generate discharged heat from the electrodes. Thus, the water is vaporized by the discharged heat, forming bubbles. These bubbles can easily be discharged with a weak electric field, to induce sudden dielectric breakdown of water. In this process, radicals, that is, hydroxyl radicals (OH), oxygen-free radicals (O—O), and hydrogen peroxide (H2O2) are generated.

The radicals generated in the above in-water discharging process oxidize metals contained in the water and also sterilize bacteria and viruses in the water while removing viral and bacterial spores at the same time.

When a discharge cell continues to be discharged after various harmful impurities in the water have been removed, the radicals accumulate in the water. Thus, the water containing the gases is given innate sterilizing properties, so that the sterilizing water can be used for various sterilizing and cleaning tasks.

However, in-water discharging apparatuses according to the related art have the following limitations.

In order to facilitate in-water discharge in the related art, miniature bubbles are introduced from the outside. That is, miniature bubbles are introduced from the outside to form an oxygenated atmosphere around the discharge electrodes, and then discharging is performed by applying a high voltage.

In another type of in-water discharging according to the related art, a needle electrode is designated as a high voltage electrode and is enclosed by a dielectric vessel such as a glass tube within a water tank, and the water inside the water tank is designated as a ground electrode. Through primary electrolysis, oxygen bubbles are generated within the dielectric vessel. Then, the bubbles fill the inside of the tank to produce an oxygenated atmosphere, and in-water discharge is performed. In this configuration, when a single needle electrode is used as a high voltage electrode for electrolysis, without oxygen being separately introduced from the outside, there is the limitation in that a large quantity of miniature bubbles cannot be generated.

Another related art in-water discharging method involves the use of a mechanical high-speed rotational spark cap for generating in-water discharge, instead of employing oxygen injection or electrolysis to generate oxygen bubbles. This method is used largely for industrial application, and has the drawback of being difficult to miniaturize for home appliances.

In related art in-water discharging methods employing electrolysis, a high voltage electrode is separated from a corresponding electrode (ground electrode), and a field strength magnifying device is provided separately to increase field strength for facilitating the generation of bubbles at the high voltage electrode. Here, electrolysis causes oxidation of the high voltage electrode, compromising the reliability of the electrode.

While in the past, humidifiers mostly generated moisture by employing ultrasound or steam, only recently have humidifiers that employ natural evaporation humidifying through the use of non-woven fabric or paper materials been commercialized.

However, related art humidifiers using the above methods have the following limitations.

First, in the case of ultrasonic humidifying, chlorosis occurs around the oscillator after prolonged use.

Also, when water is retained for a long period in a water tank without being used, impurities enter the water tank from the atmosphere and contaminate the water stored in the tank, thus presenting sanitary problems.

In the humidifying method using steam, not only are there the problems of chlorosis and sanitary problems, but considerable power is consumed in generating steam.

Moreover, humidifiers that employ ultrasonic humidification, steam humidification, and natural evaporation humidification are locally effective only. That is, humidification of regions remote from the position of the humidifier is ineffective, thus presenting the limitation in that indoor humidity cannot be uniformly maintained.

Particularly with ultrasonic humidification, when the size of atomized water particles is large, the floor around the humidifier can become wet, causing a user to slip, and mold can form on floor or wall surfaces.

Furthermore, because there are no sterilizing devices to sterilize water stored in water tanks of related art humidifiers, a separate sterilizing solution must be added when filling a water tank with water.

Also, in the case of related art humidifiers that employ natural evaporation using non-woven fabric or paper materials, the lifespan of the humidifying device is short.

Furthermore, in related art air conditioners with humidifiers, because the lifespan of the humidifying device is short, replacement intervals are short as well.

In addition, related art air conditioners are either not equipped with a separate device for performing sterilizing of a built-in humidifier, or sterilizing performance of a provided sterilizing device is inadequate.

DISCLOSURE OF INVENTION

Technical Problem

Embodiments provide an in-water discharging apparatus having a high voltage electrode and a corresponding electrode that are integrally formed, to ensure miniaturization capability and ease of installation of the discharging apparatus.

Embodiments also provide an in-water discharging apparatus that prevents oxidation of the high voltage electrode, thereby ensuring its reliability.

Embodiments further provide an in-water discharging apparatus that can be miniaturized so that the apparatus can be easily applied to electronic products such as household cooler/heaters, air cleaners, and humidifiers.

Embodiments still further provide a humidifier provided with an in-water discharging apparatus as described above.

Embodiments yet further provide a humidifier that improves upon materials of humidifying devices employed in related art natural evaporation humidifiers, to improve durability of the humidifying device and reduce power consumption.

Embodiments additionally provide an air conditioner equipped with an in-water discharging apparatus and humidifier.

Embodiments still additionally provide an air conditioning system with a humidifier provided with an in-water discharging apparatus, capable of being linked to a cooler/heater, enabling uniform indoor humidifying and circulation of indoor air.

Technical Solution

In one embodiment, an air conditioner includes: a main body including an air inlet and an air outlet; a heat exchanger within the main body; a drain pan receiving a lower end of the heat exchanger to collect condensate that forms on a surface of the heat exchanger; a fan assembly within the main body, for suctioning indoor air; and a humidifying module within the main body, and including a discharge cell that ionizes water through in-water discharging.

In another embodiment, an air conditioning system includes: an air conditioner including a fan assembly for suctioning and discharging indoor air, and a heat exchanger for performing heat exchange between air suctioned by the fan assembly and refrigerant, the air conditioner performing indoor cooling or heating; and a humidifier including a discharge cell for ionizing water through in-water discharging, a humidifying device for absorbing ionized water, and a fan assembly for suctioning and discharging air to evaporate water absorbed by the humidifying device, wherein the humidifier operates independently or in connection with the air conditioner, according to input operating conditions or an operating state of the air conditioner.

Advantageous Effects

The above-configured in-water discharging apparatus according to embodiments of the present disclosure can be manufactured with a high voltage electrode formed integrally with a corresponding electrode, so that installation is made easy and the apparatus can be miniaturized.

Also, during electrolysis for in-water discharging, oxidation of the high voltage electrode is prevented, ensuring reliability of the electrode.

Furthermore, because the in-water discharging apparatus according to embodiments of the present disclosure can be miniaturized, it can be installed in household appliances such as cooler/heaters, air cleaners, and humidifiers, thus diversifying its applications to include household appliances.

In addition, an in-water discharging apparatus according to embodiments of the present disclosure may also be applied to a water treatment apparatus in industrial field.

Also, a humidifier provided with an in-water discharging apparatus according to embodiments of the present disclosure sprays sterilized, clean water into an indoor space, promoting hygienic safety. Also, because the floor around the installed location of the humidifier is not dampened, mold formation and safety hazards for users are prevented. Additionally, water is not contaminated even when it is left for a prolonged period in the water tank, promoting hygienic safety.

Further, water supplied to a humidifier according to embodiments of the present disclosure undergoes sterilization, so that the addition of a separate sterilizing solution is not required.

Moreover, by employing a humidifying device of a ceramic material, when compared to a natural evaporation humidifier according to the related art that employs non-woven fabric or paper materials, the durability of the humidifying device is improved, and power consumption is reduced.

Also, by employing a natural evaporation method using a ceramic humidifying device, chlorosis does not occur, and the small size of humidifying particles increases their diffusion. When diffusion is improved through the small size of the humidifying particles, the problems associated with localized humidification can be overcome.

Furthermore, by using a ceramic humidifying device, the porosity is improved over a related art humidifying device made of a non-woven fiber or paper material, and thus, water absorption capability is substantially improved.

Still further, by providing a humidifier according to embodiments of the present disclosure modularized in an air conditioner, humidifying can be performed together with air conditioning. Also, by providing the humidifier as a module, indoor space utilization efficiency is improved, and a multi-function, low cost air conditioner can be manufactured.

Yet further, by linking operations of a humidifier and air conditioner according to embodiments of the present disclosure, air discharged from the air conditioner can be uniformly distributed throughout the entirety of an indoor space. Also, humidified air can also be uniformly distributed throughout the indoor space, thereby solving the problems of localized distribution.

MODE FOR THE INVENTION

Reference will now be made in detail to in-water discharging apparatuses, humidifiers provided with in-water discharging apparatuses, air conditioners provided with humidifiers, and air conditioning systems, according to embodiments of the present disclosure, examples of which are illustrated in the accompanying drawings.

The present disclosure is not limited to the embodiments and drawings disclosed herein, and shall include any substitution, modification, addition, and deletion that may be made by those skilled in the art, insofar as such changes fall within spirit and scope of the present disclosure.

Figure 1:
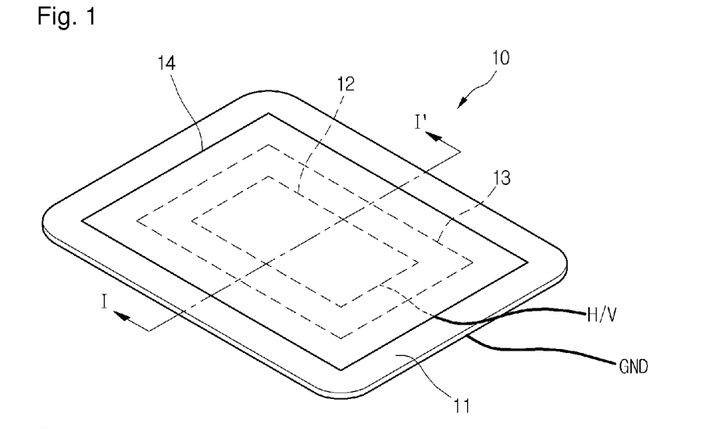
FIG. 1 is an external perspective view of an in-water discharging apparatus according to an embodiment of the present disclosure.
Figure 2:
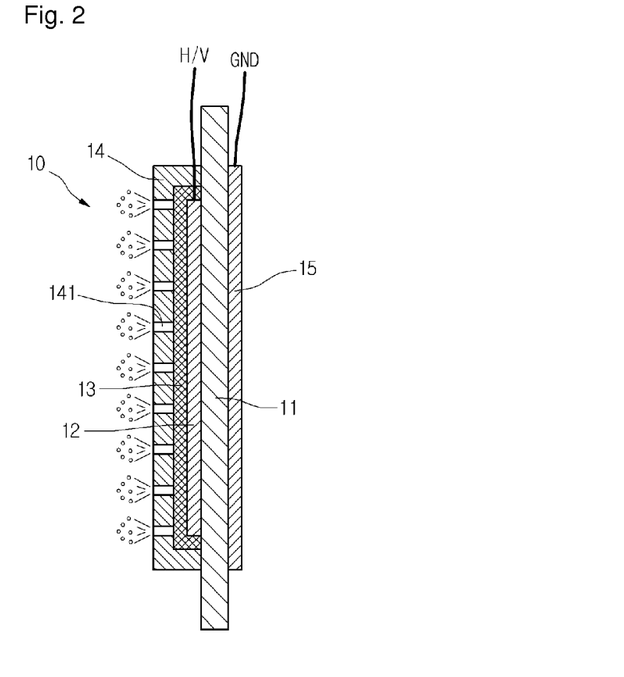
FIG. 2 is a sectional view of FIG. 1 taken along line I-I'.

FIG. 1 is an external perspective view of an in-water discharging apparatus according to an embodiment of the present disclosure, and FIG. 2 is a sectional view of FIG. 1 taken along line I-I'.

A discharge cell referred to below should be interpreted as being the same as an in-water discharging apparatus. As the principles of in-water discharging have already been described above, additional descriptions thereof will not be provided below.

Referring to FIGS. 1 and 2, a discharge cell 10 according to embodiments of the present disclosure is rectangular in shape and can be detachably mounted to any one surface of a water tank. One side surface of the discharge cell 10 constitutes a high voltage electrode surface, and the other side surface constitutes a corresponding electrode surface or, a ground electrode surface.

In detail, a discharge cell 10 according to embodiments of the present disclosure includes an insulation substrate 11 of a ceramic material, a high voltage electrode portion 12 provided on a high voltage electrode surface of the insulation substrate 11, a ground electrode portion 15 provided on a ground electrode surface, a first insulation layer 13 preventing the high voltage electrode portion 12 from contacting water and being oxidized, and a second insulation layer 14 provided on the surface of the first insulation layer 13.

In further detail, the insulation substrate 11 prevents electrical conduction between the high voltage electrode portion 12 and the ground electrode portion 15, by being an insulation layer provided between the two electrodes. Thus, the insulation substrate 11 may be formed of a ceramic material or tempered glass.

The high voltage electrode portion 12 is formed as a thin film at a micrometer thickness, through coating a metal conductive material on a surface of the insulation substrate 11. The conductive metal for the high voltage electrode portion 12 includes silver (Ag). Platinum or nickel may be used instead of silver; however, silver (having a more favorable manufacturing cost) will be described as the material in embodiments below.

The ground electrode portion 15 is formed as a thin film that coats all or a portion of the other side of the insulation substrate 11 with a metal conductive material. Power lines are connected respectively to the high voltage electrode portion 12 and the ground electrode portion 15 to apply power thereto, and a high voltage is applied momentarily through the power line connected to the high voltage electrode portion 12.

To prevent the high voltage electrode portion 12 directly contacting water and oxidizing, the surface of the high voltage electrode portion 12 is coated with ruthenium ($RuO_2$) to form a first insulation layer 13. Also, to reinforce the insulation of the high voltage electrode portion 12, a second insulation layer 14 is further formed by coating glass powder thereon.

Specifically, the coating layer of the second insulation layer 14 defines miniature voids 141, and when voltage is applied to the high voltage electrode portion 12, a considerable amount of miniature bubbles is generated through the voids 141. As the amount of miniature bubbles increases, discharging occurs at this region.

With the above-configured discharge cell 10 immersed in a water tank, when high voltage is applied to the high voltage electrode portion 12, a large quantity of miniature bubbles are generated around the voids 141 defined in the second insulation layer 14. Discharging occurs between the miniature bubbles to generate a large amount of radicals ? that is, hydroxyl radicals and active oxygen is generated. Of the generated radicals, a portion of the hydroxyl radicals recombine to generate hydrogen peroxide. Then, the radicals remove bacteria and viruses from the water.

The above-configured discharge cell 10 is very small and thin, and can thus be mounted easily on miniaturized home appliances. Installation is made even easier by the high voltage electrode and the ground electrode being integrally formed.

Figure 3:
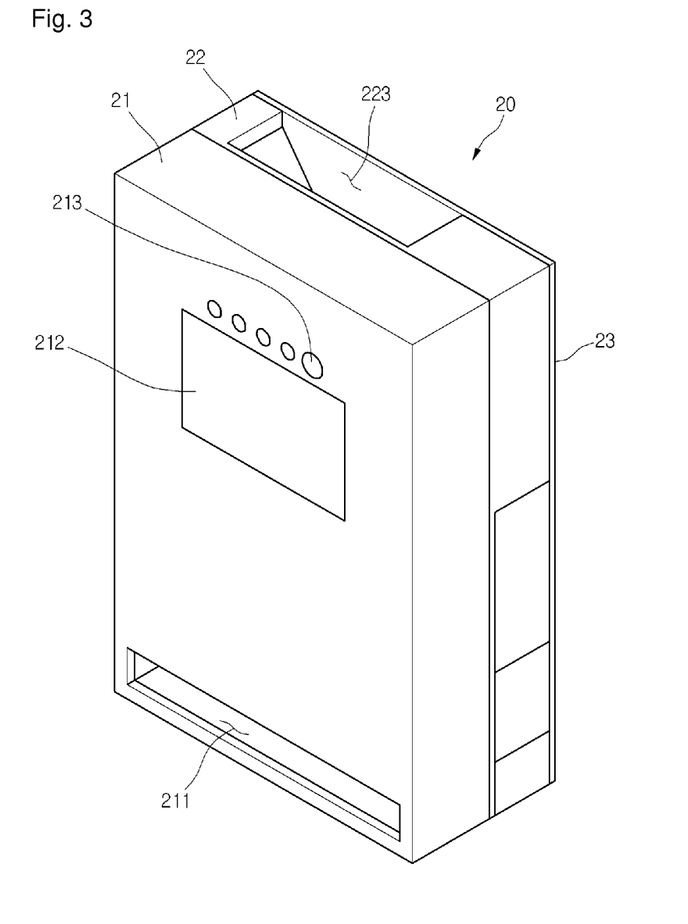
FIG. 3 is an external perspective view of a humidifier provided with an in-water discharging apparatus according to an embodiment of the present disclosure.
Figure 4:
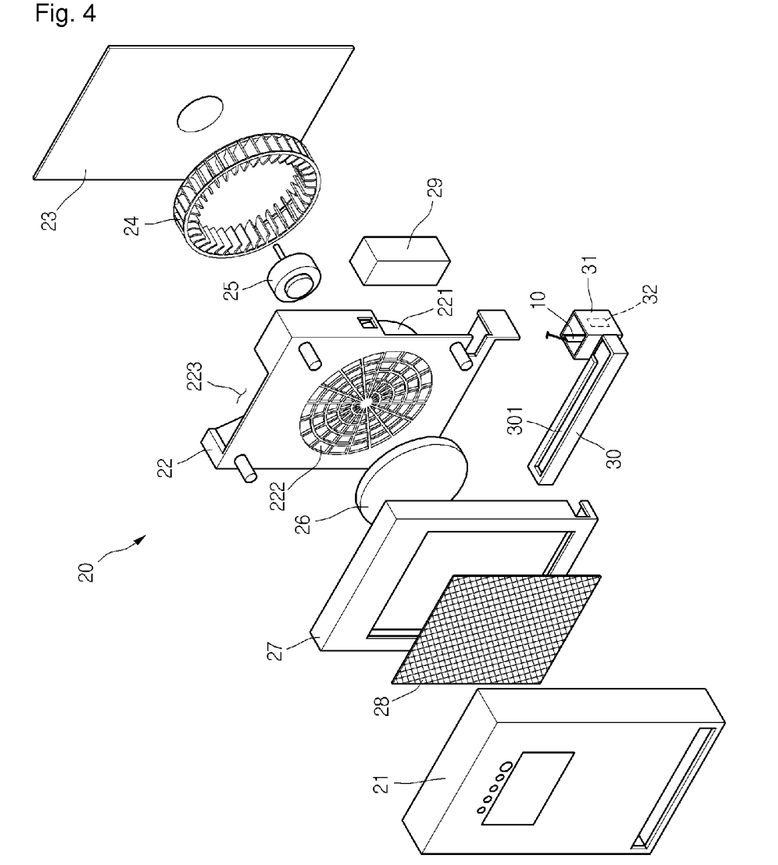
FIG. 4 is an exploded perspective view of the humidifier in FIG. 3.

FIG. 3 is an external perspective view of a humidifier provided with an in-water discharging apparatus according to an embodiment of the present disclosure, and FIG. 4 is an exploded perspective view of the humidifier in FIG. 3.

Referring to FIGS. 3 and 4, a humidifier 20, provided with an in-water discharging apparatus according to embodiments of the present disclosure, includes a front cover 21 provided with an indoor air inlet 211, a display 212, control buttons 213, etc. on its front surface, a frame 27 provided behind the front cover 21, and a filter assembly 28 mounted to the front of the frame 27 to filter dust and other impurities from indoor air.

The humidifier 20 also includes a fan housing 22 fixed at the rear of the frame 27, a fan 24 housed within the fan housing 22, a motor 25 driving the fan 24, a humidifying device 26 provided in front of the fan housing 22, and a back cover 23 covering the rear of the fan housing 22.

The humidifier 20 further includes a water tank 29 provided at a side of the fan housing 22, a container 31 provided below the water tank 29, a water pan 30 connected to the container 31 and extending underneath the humidifying device 26, a discharge cell 10 mounted on a side of the container 31, and a water level sensor 32 provided on a side of the container 31.

Specifically, indoor air is suctioned through the inlet 211 defined in a front end of the front cover 21, and the suctioned indoor air passes through the filter assembly 28 and is guided to the humidifying device 26.

The filter assembly 28 mounted at the front of the frame 27 performs the function of removing dust, odor particles, and bacteria from air, and may have different types of filtering members arranged sequentially to filter air in stages. That is, at least two or more of a pre-filter for filtering larger impurities from air, a high performance HEPA filter for filtering finer dust particles, a nano-filter with superb sterilizing performance for removing odors, optional filters such as a yellow dust filter and an odor filter selectively installed, a hybrid filter with a plurality of polyurethane or other non-woven materials with different flow consistencies, and a plasma electrical discharge unit for ionizing and collecting dust, may be arranged from front-to-rear.

The inner portion of the frame 27 is open, and the filter assembly 28 is mounted on the open portion. The fan housing 22 is fixed and mounted to the rear of the frame 27.

The humidifying device 26 is formed as a ceramic device, which has superior water absorbency compared to related art humidifying devices formed of non-woven materials. The material and structure of the humidifying device 26 will be described in further detail below with reference to the drawings.

The fan housing 22 includes an air guide 221 to guide the direction in which suctioned indoor air is discharged, and a grill 222 provided at an inlet formed at the front of the air guide 221. The humidifying device 26 is disposed at the front of the grill 222. A plurality of ribs may be provided in a lattice configuration on the grill 222. The fan 24 mounted within the fan housing 22 may be a centrifugal fan that discharges air in a radial direction. That is, a turbo fan or a scirocco fan may be employed. An outlet 223 is defined at the top of the fan housing 22 so that air that passes through the humidifying device 26 and absorbs moisture can be discharged to the indoor environment. In detail, the outlet 223 is designed to be directed upward and slightly forward from the humidifier 20, so that moist air can be discharged at a predetermined angle upward and at a predetermined slope from a horizontal plane. Thus, airflow that is discharged through the outlet 223 can be uniformly circulated in an indoor space. In addition, when an air cooler/heater is installed at the wall opposite to the humidifier 20, circulation of air can be improved.

A water pan 30 is provided at the lower front of the fan housing 22, such that the container 31 that stores water sterilized through in-water discharging is connected to the one end of the water pan 30.

In detail, a groove 301 of a predetermined depth is defined in the top of the water pan 30, and the floor of the groove 301 may be either horizontally formed or sloped so that the groove 301 becomes deeper in a direction away from the container 31. A portion at the bottom of the humidifying device 26 is received in the groove 301 and is immersed in the water that enters the groove 301. Thus, the water absorbed from the bottom of the humidifying device 26 is transferred upward.

The water tank 29 is connected to the top of the container 31, and a solenoid valve may be installed in an outlet defined at the bottom of the water tank 29. The discharge cell 10 is mounted on an inner side surface of the container 31 to ionize water supplied to the container 31 through in-water discharging. The water level sensor 32 may be mounted on the opposite inner surface of the container 31. Accordingly, the solenoid valve may selectively be driven according to the amount of water sensed within the container 31 by the water level sensor 32, to maintain an adequate supply of water to the container 31.

Figure 5:
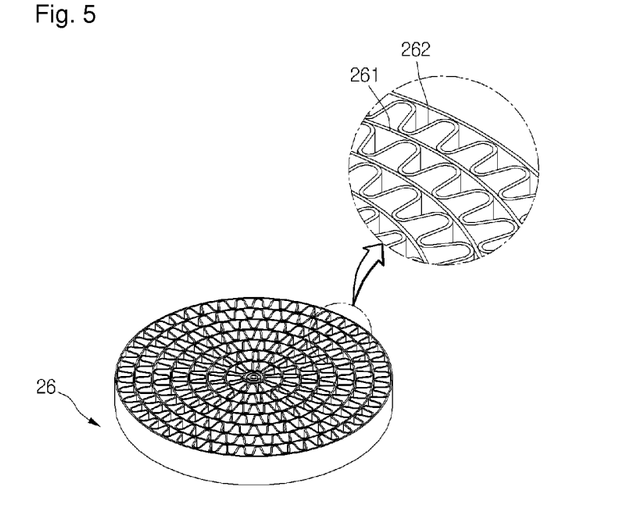
FIG. 5 is a perspective view of a humidifying device according to an embodiment of the present disclosure.

FIG. 5 is a perspective view of a humidifying device according to an embodiment of the present disclosure.

Referring to FIG. 5, the humidifying device 26 according to embodiments of the present disclosure is a water absorbing device formed of the materials alumina (Al2O3), silica (SiO2), and zirconia (ZrO2) in a ratio of 38:47:15.

Specifically, the humidifying device 26 is formed of a rectangular flat base 261, and a corrugated plate 262 with a plurality of rounded corrugations provided on the base 261. Indoor air passes through spaces between the corrugations of the corrugated plate 262 and is guided to the fan housing 22. As the air passes through the spaces formed between the corrugations, moisture absorbed in the base 261 and the corrugated plate 262 evaporates.

While the spaces between the corrugations are depicted in the diagram as being wide, in actuality, the corrugated spaces are tightly connected. The average span of the spaces in the humidifying device 26 is approximately 17-18 microns.

Figure 6:
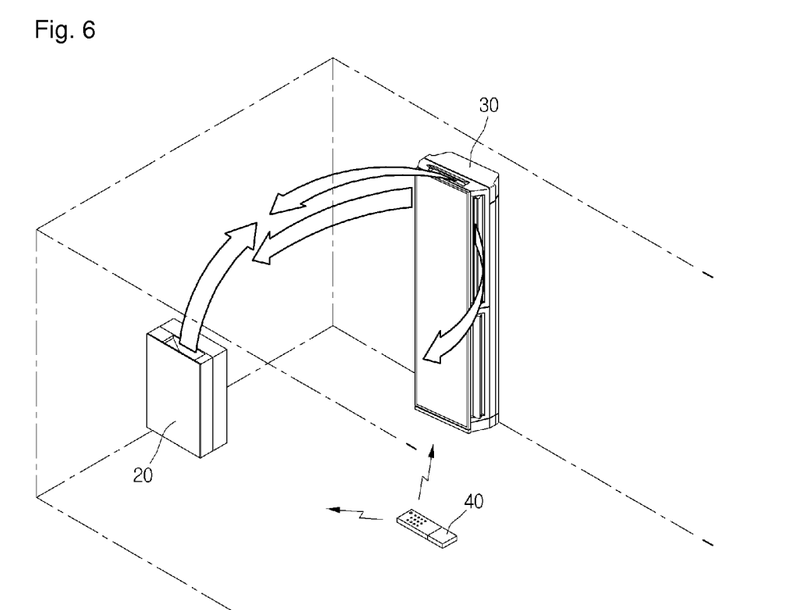
FIG. 6 is an air conditioning system installation diagram with a humidifier and an air conditioner according to embodiments of the present disclosure.
Figure 7:
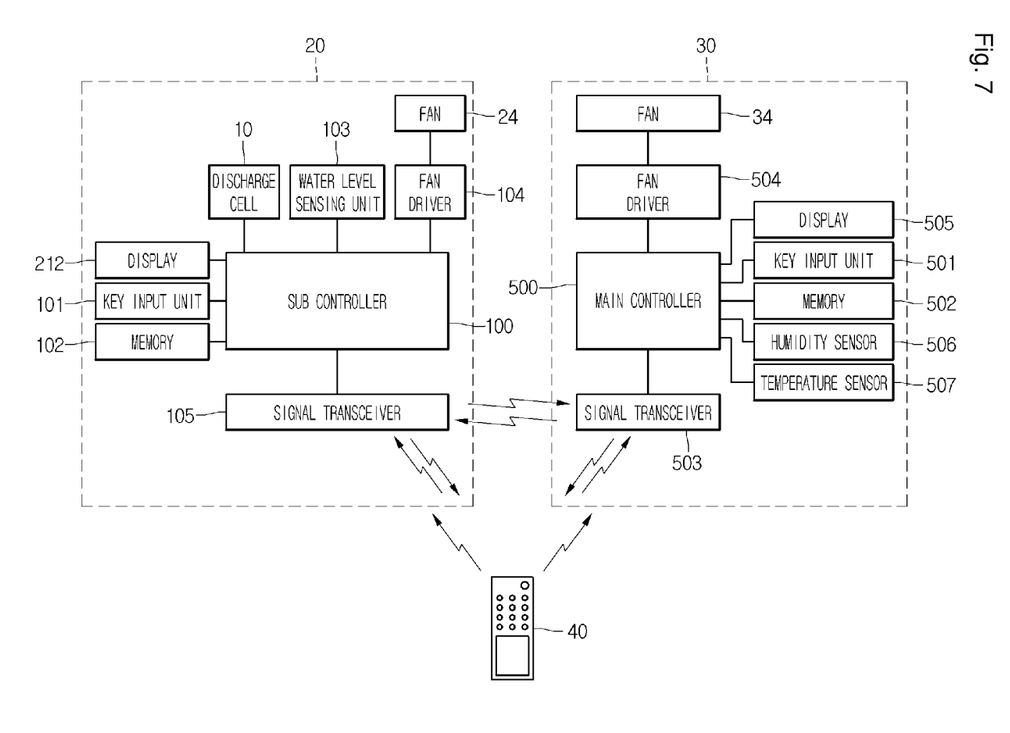
FIG. 7 is a block diagram showing the control configuration of the air conditioning system in FIG. 6.

FIG. 6 is an air conditioning system installation diagram with a humidifier and an air conditioner according to embodiments of the present disclosure, and FIG. 7 is a block diagram showing the control configuration of the air conditioning system in FIG. 6.

Referring to FIGS. 6 and 7, a humidifier provided with an in-water discharging apparatus according to embodiments of the present disclosure may be linked to an air conditioner.

In detail, the humidifier 20 may be mounted on a wall at one side of an indoor space, and the air conditioner 30 may be installed at the wall opposite to where the humidifier 20 is installed. Here, the air conditioner 30 may be a cooler/heater air conditioner with an air conditioning unit that performs cooling and a hot blast heater that performs heating, and may also include an air cleaner. The air conditioner may be a wall mounted unit that mounts on a wall, an integrated air conditioner with integrated indoor and outdoor units that is installed through a wall (or window), a ceiling mounted unit that mounts on a ceiling, or a floor-ducted air conditioning system with ducts installed in the floor. The humidifier 20 may be installed to be disposed a predetermined height off the floor. As described above, the moist air discharged through the outlet of the humidifier 20 is discharged toward the region in which the cooler/heater is installed, to better circulate air indoors. Thus, not only is humidifying performed by the humidifier 20, but the humidifier 20 also aids in performing an air circulation function.

With the use of a remote controller, an operating mode of only the humidifier 20, an operating mode of only the air conditioner 30, or an operating mode of both the humidifier 20 and the air conditioner 30 may be selected. Additionally, the controllers of the air conditioner 30 and the humidifier 20 may be electrically connected, enabling the operating mode of the humidifier 20 to vary according to the operating mode of the air conditioner 30. For example, when the airflow volume of the air conditioner 30 and the level of indoor air humidity sensed by a humidity sensor (not shown) provided at a side of the air conditioner 30 are designated as determining factors, the operating conditions of the humidifier 20 may be made variable accordingly.

Below, the controlling configuration of the air conditioning system will be described.

Here, for descriptive convenience, the controller of the air conditioner 30 is designated as a main controller 500, and the controller of the humidifier 20 is designated as a sub controller 100.

In detail, the humidifier 20 includes the sub controller 100, a key input unit 101 for inputting operating conditions for the humidifier 20, a signal transceiver 105 for transmitting and receiving signals to and from the main controller 500 and a remote control 40, a memory 102 for storing various data including data received through the signal transceiver 105 and data for determining operating conditions of the humidifier 20, a water level sensing unit 103 for sensing the water level inside the container 31, a fan driver 104 for driving the fan 24, a display 212 for displaying the operating state of the humidifier 20, and a discharge cell 10 whose operation is controlled by the sub controller 100.

In further detail, the key input unit 101 includes the control buttons 213 described with reference to FIG. 3, and the fan driver 104 includes the motor 25 described with reference to FIG. 3. Also, the water level sensor 32 described with reference to FIG. 3 is included in the water level sensing unit 103.

The air conditioner 30 includes the main controller 500, a signal transceiver 503, a fan driver 504, a fan 34 (in FIG. 9) that operates according to a signal received by the fan driver 504, a memory 502, a key input unit 501, and a display 505.

In detail, the elements with the same nomenclatures as those of the humidifier 20 perform the same functions pertaining to the operation of the air conditioner 30, and thus, repetitive descriptions will not be provided.

Here, the signal transceivers 105 and 503 and the remote control 40 perform wireless communication through infrared transmission/reception, radio frequency (RF) wireless communication, Bluetooth, etc.

The main controller 500 of the air conditioner 30 may include a humidity sensor 506 for sensing indoor humidity and a temperature sensor 507 for sensing room temperature, that are electrically connected.

In the above-configured air conditioning system, a user can manually input operating conditions through the key input units 101 and 501 into the humidifier 20 and the air conditioner 30, respectively. Also, sole operation of the humidifier 20 and the air conditioner 30, or linked operation may be selected. In another method, the remote control 40 may be used to wirelessly input operating conditions into the humidifier 20 and the air conditioner 30.

If the sub controller 100 of the humidifier 20 and the main controller 500 of the air conditioner 30 are electrically connected, operating data can be transmitted and received wirelessly through the signal transceivers 105 and 503. Accordingly, data on the operating state of the air conditioner 30 may be transmitted to the signal transceiver 105 of the humidifier 20, and the transmitted data may be input to the sub controller 100. Also, required data may be uploaded by the controller 100 from the memory 102, and the uploaded data may be compared to data transmitted from the air conditioner 30 to determine how to vary the operation of the humidifier 20. That is, without a user's inputted commands, the operating conditions of the humidifier 20 may be automatically adjusted according to the operating state of the air conditioner 30 and the state of indoor air.

In one example, the operating conditions of the humidifier 20 with respect to the operating state of the air conditioner 30 may be stored in the memories 102 and 502 as shown in Table 1 below.

TABLE 1

| Indoor Temperature (° C.) | Indoor Humidity (%) | Airflow Volume (m³/hour) | Humidifer Fan Speed (rpm) |
|---|---|---|---|
| 20~25 | 71~80 | Extra High | a |
| | | | b |
| | | | c |
| | | High | d |
| | | | e |
| | | | f |
| | | Medium | g |
| | | | h |
| | | | i |
| | | Low | j |
| | | | k |
| | | | l |
| | 60~70 | Extra High | : |
| | | | : |

Table 1 above partially shows a data table for determining the fan speed of a humidifier according to indoor temperature, indoor humidity, and airflow volume of an operating air conditioner.

In other words, indoor humidity will be varied in distribution within a certain temperature range, and the operable states of the air conditioner will fall within certain humidity parameters from a number of percentage ranges of indoor humidity. Also, the fan speed of the humidifier is set according to which operating state the air conditioner is in. Also, the data in Table 1 may be stored in the memory 502 of the air conditioner 30 and/or the memory 102 of the humidifier 20.

According to Table 1, the fan speed of the humidifier is automatically determined when the current indoor temperature and indoor humidity, and the operating state (airflow volume) of the air conditioner are determined.

For example, data on the current indoor temperature, indoor humidity, and airflow volume of the air conditioner 30 is transmitted by the main controller 500 through the signal transceiver 503 to the signal transceiver 105 of the humidifier 20. Then, the sub controller 100 of the humidifier 20 receives the data and uploads the data from Table 1 from the memory 102 to generate a fan speed. Then, the sub controller 100 transmits a drive signal to the fan driver 104 in accordance with the generated fan speed, and the fan driver 104 drives and rotates the fan 24 at the set speed.

In Table 1 above, one example has been given to show in general how the humidifier 20 can be linked in operation with the air conditioner 30; however, various types of data values may be determined according to operation modes. That is, the indoor temperature and indoor humidity may have set ranges and not be referenced, or fine adjustments may be made according to predetermined indoor temperatures.

Figure 8:
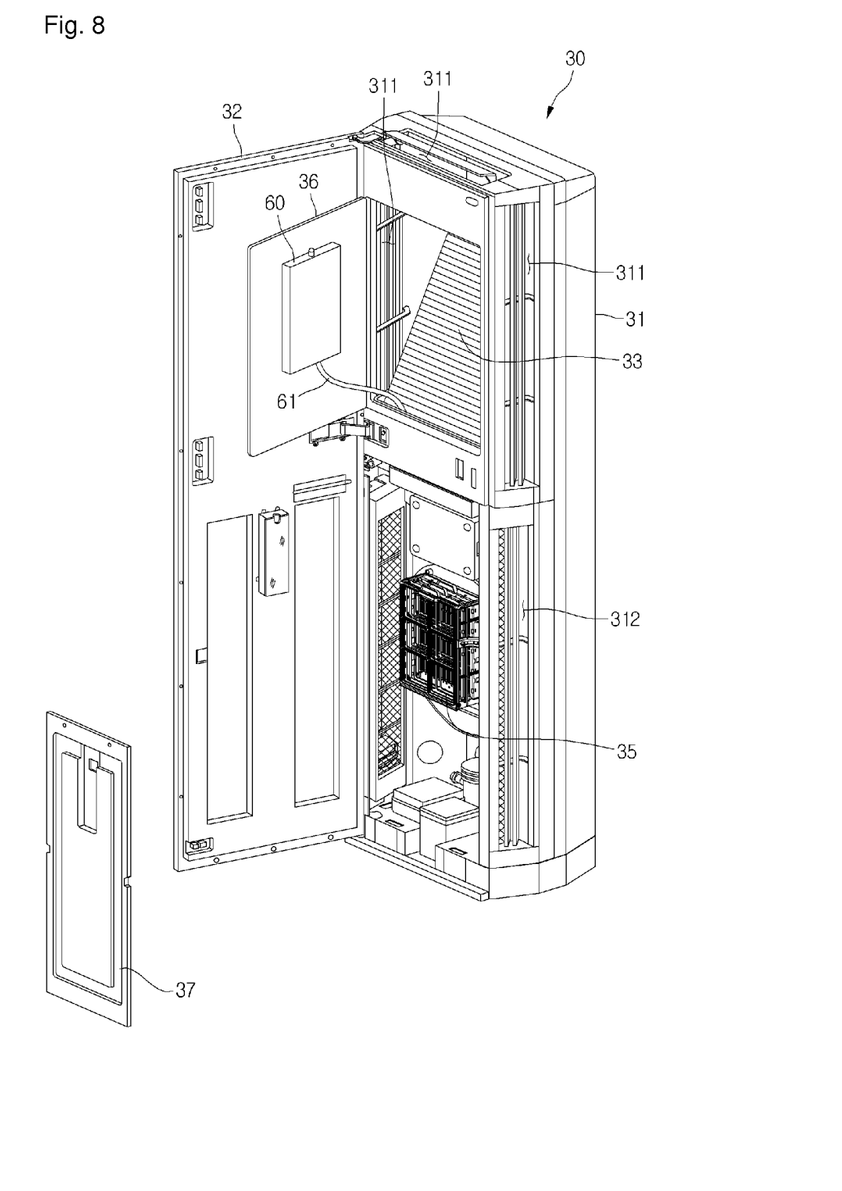
FIG. 8 is a perspective view of an air conditioner provided with a humidifier according to embodiments of the present disclosure.
Figure 9:
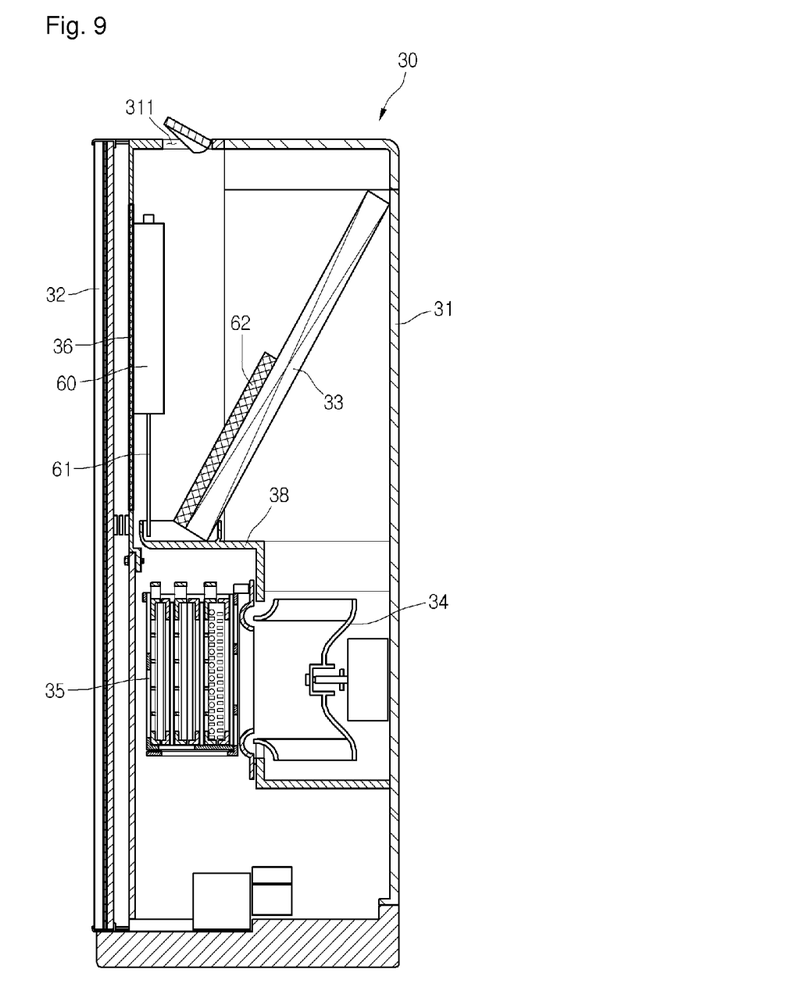
FIG. 9 is a side sectional view of the air conditioner in FIG. 8.
Figure 10:
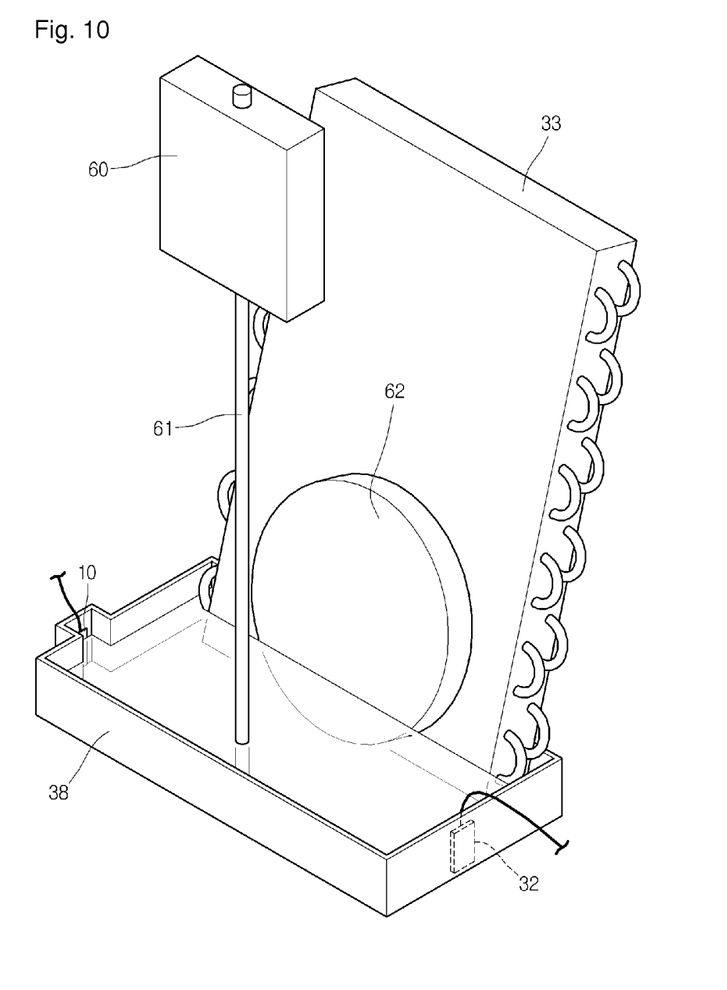
FIG. 10 is an enlarged perspective view showing an in-water discharging apparatus and a humidifier installed in an air conditioner.

FIG. 8 is a perspective view of an air conditioner provided with a humidifier according to embodiments of the present disclosure, FIG. 9 is a side sectional view of the air conditioner in FIG. 8, and FIG. 10 is an enlarged perspective view showing an in-water discharging apparatus and a humidifier installed in an air conditioner.

Referring to FIGS. 8 to 10, in the present embodiments, the in-water discharging apparatus and the humidifier are integrated in one module and provided inside an air conditioner 30.

In detail, the air conditioner 30 includes a main body 31 constituting its exterior, a front panel 32 pivotably provided at the front of the main body 31, a heat exchanger 33 mounted in the upper portion of the main body 31, a drain pan 38 supporting the bottom of the heat exchanger 33, a fan assembly 34 for suctioning indoor air provided below the heat exchanger 33, and a filter assembly 35 provided at the front of the fan assembly 34. The filter assembly 35 may be the same filter assembly provided on the humidifier 20.

An inner cover 36 and sealing cover 37 are provided between the main body 31 and front panel 32 to prevent inner components from being exposed when the front panel 32 is opened. Inlets 312 through which indoor air is suctioned are defined in either side at lower portions of the main body 31, and outlets 311 are defined at upper portions thereof. Also, an outlet 311 may further be defined in the front portion at the top of the main body 31. The inlets 312 and outlets 311 are selectively opened and closed by louvers.

The inner cover 36 is provided to pivot about a side thereof, and a water tank 60 for humidifying is mounted on the rear surface of the inner cover 36. A humidifying device 62 that is the same as the humidifying device provided in the humidifier 20 is seated on the front surface of the heat exchanger 33. The lower end of the humidifying device 62 is maintained immersed in water accumulated in the drain pan 38. A tube 61 extends from the lower end of the water tank 60 to the floor of the drain pan 38. The discharge cell 10 is mounted to a side of the drain pan 38, and a water level sensor 32 is mounted on the other side thereof. A solenoid valve (not shown) is installed at the entrance of the tube 61 to selectively open or seal the tube 61 according to a value sensed through the water level sensor 32. That is, a set water level of the drain pan 38 can be attained with only condensate that descends from the surface of the heat exchanger 33, so that there is no need to supply water from the water tank 60. In other cases, the solenoid valve can open to admit water supplied from the water tank 60. For example, because condensate does not form when the air conditioner 30 is operated in heating mode, water must be supplied to the drain pan 38 from the water tank 60 during heating mode.

A cover is provided on the top of the water tank 60, allowing a user to directly fill the water tank 60 by opening the inner cover 36. The water tank 60 may be made detachable from the inner cover 36.

Another method is to directly connect an external water supply pipe to the water tank 60.

Specifically, a separate water level sensor may be provided inside the water tank 60, and a separate solenoid valve may be installed at the connecting portion of the water tank 60 to which the external water supply pipe extends. Thus, water may selectively be supplied through the external water supply pipe according to the water level inside the water tank 60.

As described above, by providing the discharge cell 10, humidifying device 62, and water tank 60 inside the air conditioner, humidifying may be performed together with cooling or heating. Additionally, when humidifying is not required, the water accumulated in the drain pan 38 may be drained. For this purpose, a drain pump may be mounted to an inner portion of the air conditioner 30 to drain the water in the drain pan 38. Of course, any method of naturally draining the drain pan without employing a drain pump can be applied instead.

Through the above configuration, condensate generated on the heat exchanger 33 may be used to control the humidity of indoor air, thus enabling the condensate to be used.

Also, the water accumulated in the drain pan 38 is sterilized by the discharge cell 10, so that moist air supplied to the indoor space can be maintained in a clean and sterile state.

Here, the humidifying device 62 and the discharge cell 10 may not be provided in the drain pan 38, and a separate water pan may be provided separated a predetermined height above the drain pan 38. That is, the humidifying device 62 and the discharge cell 10 may be provided with a separate water pan, and the water tank 60 may be connected through a tube to the water pan.

By providing the humidifier and in-water discharging apparatus as a single module inside the air conditioner 30, there is no need for a separate humidifier.

The invention claimed is:

1. An air conditioner, comprising:
a main body comprising an air inlet and an air outlet;
a heat exchanger provided within the main body;
a drain pan mounted at a lower side of the heat exchanger to collect condensate that forms on a surface of the heat exchanger;
a fan assembly mounted within the main body that suctions an indoor air;
an inner cover that is rotatably coupled to the main body and includes a surface on which a water tank that supplies water to the drain pan is mounted;
a humidifying device disposed on a surface of the heat exchanger, wherein a lower portion of the humidifying device is immersed in water accumulated in the drain pan; and
a discharge cell mounted to an inner side of the drain pan, wherein the discharge cell includes opposed surfaces on which a high voltage electrode portion and a ground electrode portion are installed, respectively, a first insulation layer disposed on the high voltage electrode portion that prevents the high voltage electrode portion from contacting water and being oxidized, and a second insulation layer disposed on the first insulation layer and including a plurality of voids, and wherein when a voltage is applied to the high voltage electrode portion, a plurality of bubbles is generated through the plurality of voids.

2. The air conditioner according to claim 1, wherein the water tank comprises an intermediate member at one end thereof to supply water, or the water tank is directly connected to a tap water pipe.

3. The air conditioner according to claim 1, wherein the drain pan comprises a water level sensor mounted at one side thereof, and wherein a quantity of water supplied from the water tank is controlled according to a water level sensed by the water level sensor.

4. The air conditioner according to claim 1, wherein the humidifying device is disposed in a passage for air discharged from the fan assembly.

5. The air conditioner according to claim 1, wherein the humidifying device is formed of a ceramic material.

6. The air conditioner according to claim 1, wherein the opposed surfaces of the discharge cell are formed on opposite surfaces of a substrate, respectively.

7. The air conditioner according to claim 6, wherein the high voltage electrode portion is formed of a thin film of a conductive metal on a surface of the substrate opposite to the ground electrode portion of the substrate.

8. The air conditioner according to claim 6, wherein the substrate is formed of ceramic or glass, and wherein high voltage electrode portion is formed on one side of the substrate and the ground electrode portion is formed at the other side of the substrate.

9. The air conditioner according to claim 1, further comprising a filter assembly disposed at a front of the fan assembly that filters the suctioned indoor air when the suctioned indoor air passes through the filter assembly.

10. The air conditioner according to claim 9, wherein the filter assembly includes a plurality of filters, and wherein the plurality of filters includes two or more selected from a pre-filter that removes larger impurities, a fine filter that removes fine dust particles, an odor filter that removes odor, yellow dust filter, a hybrid filter including a plurality of polyurethane or other non-woven materials having different flow consistencies, and a plasma electric discharge device that ionizes and collects dust.

* * * * *